(12) United States Patent
Uda et al.

(10) Patent No.: US 12,352,764 B2
(45) Date of Patent: Jul. 8, 2025

(54) METHOD OF DETECTING HEART FAILURE, DEVICE FOR DETECTING HEART FAILURE, SANDWICH IMMUNOASSAY METHOD, AND COMBINATION OF ANTIBODIES

(71) Applicant: KYORITSU SEIYAKU CORPORATION, Tokyo (JP)

(72) Inventors: Tomohiko Uda, Ibaraki (JP); Saeko Kitayama, Ibaraki (JP); Kenyo Ishii, Ibaraki (JP)

(73) Assignee: KYORITSU SEIYAKU CORPORATION, Tokyo (JP)

( * ) Notice: Subject to any disclaimer, the term of this patent is extended or adjusted under 35 U.S.C. 154(b) by 553 days.

(21) Appl. No.: 17/046,819

(22) PCT Filed: Apr. 12, 2019

(86) PCT No.: PCT/JP2019/015992
§ 371 (c)(1),
(2) Date: Oct. 12, 2020

(87) PCT Pub. No.: WO2019/198822
PCT Pub. Date: Oct. 17, 2019

(65) Prior Publication Data
US 2021/0148934 A1 May 20, 2021

(30) Foreign Application Priority Data
Apr. 13, 2018 (JP) ................................. 2018-077708

(51) Int. Cl.
*G01N 33/68* (2006.01)
*G01N 33/543* (2006.01)

(52) U.S. Cl.
CPC ... *G01N 33/6893* (2013.01); *G01N 33/54306* (2013.01); *G01N 2333/58* (2013.01); *G01N 2800/325* (2013.01)

(58) Field of Classification Search
None
See application file for complete search history.

(56) References Cited

U.S. PATENT DOCUMENTS

2014/0302534 A1\* 10/2014 Kojima .................. G01N 33/58
530/387.9

FOREIGN PATENT DOCUMENTS

| JP | H8-226919 | 9/1996 |
|---|---|---|
| JP | 2006-523298 | 10/2006 |

(Continued)

OTHER PUBLICATIONS

GenScript (Sandwich Elisa principles, formats and Optimization, 2016) (Year: 2016).*

(Continued)

*Primary Examiner* — Bao-Thuy L Nguyen
*Assistant Examiner* — Chau N. B. Tran
(74) *Attorney, Agent, or Firm* — Jeffrey S. Melcher; Melcher Patent Law PLLC

(57) ABSTRACT

[Problem]
To provide means for detecting heart failure more simply and highly accurately.
[Solution Means]
A method of detecting heart failure from a sample collected from an organism, the method comprising the step of: performing sandwich immunoassay of NT-proANP or a fragment thereof contained in the sample using a first antibody for capturing for which an epitope lies on any site among positions 31 to 67 of an amino acid sequence of NT-proANP and a second antibody for labeling for which an (Continued)

epitope lies on any site among positions 31 to 67 of the amino acid sequence of NT-proANP, and the like.

The epitopes of the two types of antibodies: one for capturing and the other for labeling, both of which lie among positions 31 to 67 of the amino acid sequence of NT-proANP. This, therefore, enables detention of a fragment having the same amount of substance as NT-proANP and simple and highly accurate detection of heart failure, even if NT-proANP is further cleaved and decomposed into 3 pieces during circulation in blood.

10 Claims, 2 Drawing Sheets

Specification includes a Sequence Listing.

(56) References Cited

FOREIGN PATENT DOCUMENTS

| | | |
|---|---|---|
| JP | 2014-210761 | 11/2014 |
| JP | 5675346 | 2/2015 |

OTHER PUBLICATIONS

Janeway et al.(Immunobiology: the Immune System in Health and Disease (2001), Elsevier Science Ltd/Garland Publishing, New York, NY, Fifth Edition, sections 3-6 and 3-7 (Year: 2001) (Year: 2001).*

Almagro et al. Humanization of Antibodies, Frontiers in Bioscience 13, 1619-1633, 2008 (Year: 2008) (Year: 2008).*

Goel et al. "Plasticity within the Antigen Combining Site May Manifest as Molecular Mimicry in the Humoral Immune Response", The Journal of Immunology 173(12):7358-7367, 2004 (Year: 2004) (Year: 2004).*

Edwards et al. The remarkable flexibility of the human antibody repertoire; isolation of over one thousand different antibodies to a single protein, BLyS, J. Mol. Biol. (2003) 334, 103-118, DOI: 10.1016/j.jmb.2003.09.054 (Year: 2003) (Year: 2003).*

Lloyd et al. Modelling the human immune response: performance of a 10e11 human antibody repertoire against a broad panel of therapeutically relevant antigens, Protein Engineering, Design and Selection, vol. 22, Issue 3, Mar. 1, 2009, pp. 159-168, https://doi.org/10.1093/protein/gzn058 (Year: 2009) (Year: 2009).*

Brown et al. Tolerance of single, but not multiple, amino acid replacements in antibody VH CDR 2: a means of minimizing B cell wastage from somatic hypermutation?, J Immunol. May 1996;156(9):3285-91 (Year: 1996) (Year: 1996).*

Vajdos et al. Comprehensive functional maps of the antigen-binding site of an anti-ErbB2 antibody obtained with shotgun scanning mutagenesis, J Mol Biol. Jul. 5, 2002;320(2):415-28, DOI: 10.1016/S0022-2836(02)00264-4 (Year: 2002) (Year: 2002).*

Boswood et al. (Clinical validation of a proANP 31-67 fragment Elisa in the diagnosis of heart failure in the dog, Journal of small animal practice, 2003 44, 104-108) (Year: 2003).*

International Search Report issued in PCT/JP2019/015992, Jul. 30, 2019, pp. 1-3.

Written Opinion issued in PCT/JP2019/0159922, Jul. 30, 2019, pp. 1-4.

Daggubati, s. et al., Adrenomedullin, endothelin, neuropeptide Y, atrial, brain, and C-natriuretic prohormone peptides compared as early heart failure indicators, Cardiovascular Research, 1997, vol. 36, pp. 246-255.

Boswood, A. et al., Clinical validation of a proANP 31-67 fragment Elisa in the diagnosis of heart failure in the dog, Journal of Small Animal Practice, vol. 44, 2003, pp. 104-108.

Haggstrom, J. et al., Relationship between different natriuretic peptides and severity of naturally acquired mitral regurgitation in dogs with chronic myxomatous valve disease, Journal of Veterinary Cardiology, vol. 2, No. 1, May 2000, pp. 7-16.

Hori, Y. et al., Clinical implications of measurement of plasma atrial natriuretic peptide concentration in dogs with spontaneous heart disease, Journal of the American Veterinary Medical Association, Oct. 15, 2011, vol. 239, No. 8, pp. 1077-1083.

Sreedevi Daggubati, James R. Parks, Rose M. Overton, Guillermo Cintron, Douglas D. Schocken, David L. Vesely, "Adrenomedullin, endothelin, neuropeptide Y, atrial, brain, and C-natriuretic prohormone peptides compared as early heart failure indicators". Cardiovascular Research (36)246-255, 1997.

* cited by examiner

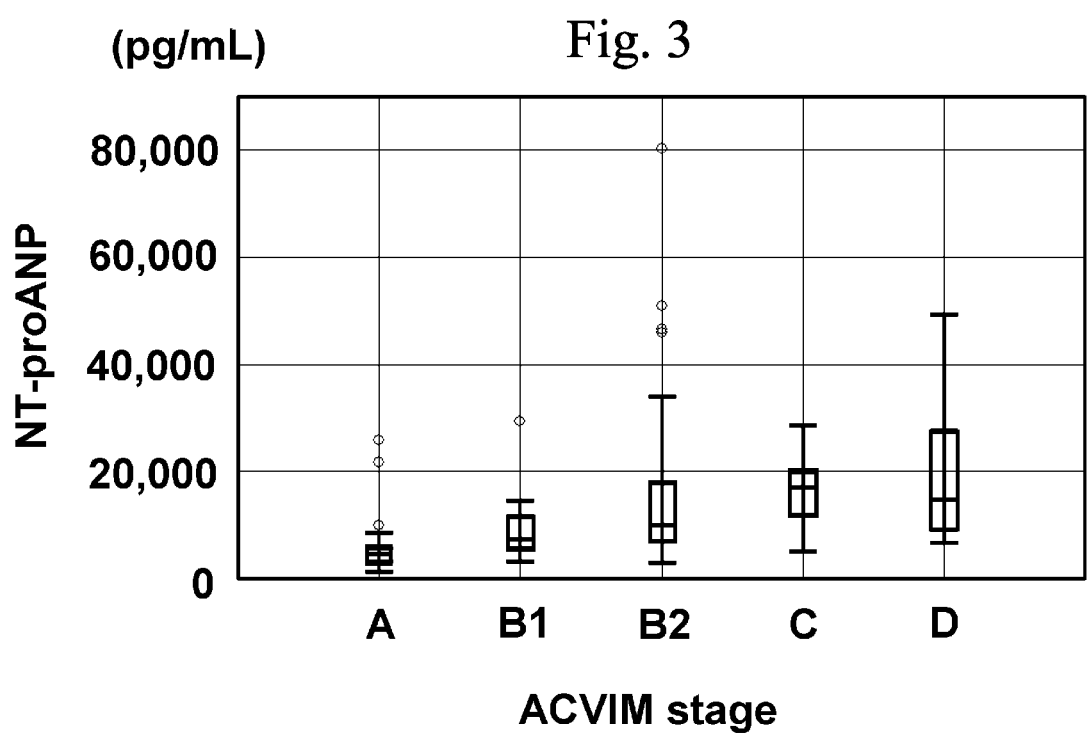

SEQUENCE LISTING

<160> NUMBER OF SEQ ID NOS: 30

<210> SEQ ID NO 1
<211> LENGTH: 357
<212> TYPE: DNA
<213> ORGANISM: Mus musculus

<400> SEQUENCE: 1
gaggtgcagc tggtggagtc tgggggaggc ttagtgaagc ctggagggtc cctgaaactc    60
tcctgtgcag cctctggatt cactttcagt agctatgcca tgtcttgggt tcgccagact   120
ccggagaaga ggctggaatg ggtcgcaacc attagtactg gtggtagttt cgcctactat   180
acagacagta tgaagggtcg attcatcatc tccagagaca tgccaagaac acccctgtcc   240
ctgcagatga gcagtctgag gtctgaggac acggccatct attactgttc aagacatgat   300
ggagataaga cctggtttgc tgactggggc caagggactc tggtcactgt ctctgca      357

<210> SEQ ID NO 2
<211> LENGTH: 119
<212> TYPE: PRT
<213> ORGANISM: Mus musculus

<400> SEQUENCE: 2

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Thr Gly Gly Ser Phe Ala Tyr Tyr Thr Asp Ser Met
    50                  55                  60

Lys Gly Arg Phe Ile Ile Ser Arg Asp Asn Ala Lys Asn Thr Leu Ser
65                  70                  75                  80

Leu Gln Met Ser Ser Leu Arg Ser Glu Asp Thr Ala Ile Tyr Tyr Cys
                85                  90                  95

Ser Arg His Asp Gly Asp Lys Thr Trp Phe Ala Asp Trp Gly Gln Gly
            100                 105                 110

Thr Leu Val Thr Val Ser Ala
        115

<210> SEQ ID NO 3
<211> LENGTH: 336
<212> TYPE: DNA
<213> ORGANISM: Mus musculus

<400> SEQUENCE: 3
gatgttgtgg tgacccaaac tccactctcc ctgcctgtca gtcttggaga tcaagcctcc    60
atctcttgca gatctagtca gagccttgta cacagtaatg aaacacccta tttacattgg   120
tacctacaga agccaggcca gtctccaaag ctcctgatct acaaagtttc caaccgattc   180
tctggggtcc cagacaggtt cagtggcagt ggatcaggga cagatttcac actcaagatc   240
agtagagtgg aggctgagga tctgggagtt tatttctgct ctcaaagtac acttttccg    300 tacacgttcg gaggggggac caagctggaa ataaaa                             336

<210> SEQ ID NO 4
<211> LENGTH: 112
<212> TYPE: PRT
<213> ORGANISM: Mus musculus

<400> SEQUENCE: 4

Asp Val Val Val Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

```
Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr Leu Phe Pro Tyr Thr Phe Gly Gly Gly Thr Lys Leu Glu Ile Lys
            100                 105                 110

<210> SEQ ID NO 5
<211> LENGTH: 10
<212> TYPE: PRT
<213> ORGANISM: Mus musculus

<400> SEQUENCE: 5

Gly Phe Thr Phe Ser Ser Tyr Ala Met Ser
1               5                   10

<210> SEQ ID NO 6
<211> LENGTH: 17
<212> TYPE: PRT
<213> ORGANISM: Mus musculus

<400> SEQUENCE: 6

Thr Ile Ser Thr Gly Gly Ser Phe Ala Tyr Tyr Thr Asp Ser Met Lys
1               5                   10                  15

Gly

<210> SEQ ID NO 7
<211> LENGTH: 10
<212> TYPE: PRT
<213> ORGANISM: Mus musculus

<400> SEQUENCE: 7

His Asp Gly Asp Lys Thr Trp Phe Ala Asp
1               5                   10

<210> SEQ ID NO 8
<211> LENGTH: 16
<212> TYPE: PRT
<213> ORGANISM: Mus musculus

<400> SEQUENCE: 8

Arg Ser Ser Gln Ser Leu Val His Ser Asn Gly Asn Thr Tyr Leu His
1               5                   10                  15

<210> SEQ ID NO 9
<211> LENGTH: 7
<212> TYPE: PRT
<213> ORGANISM: Mus musculus

<400> SEQUENCE: 9

Lys Val Ser Asn Arg Phe Ser
1               5

<210> SEQ ID NO 10
<211> LENGTH: 9
<212> TYPE: PRT
<213> ORGANISM: Mus musculus

<400> SEQUENCE: 10
```

Ser Gln Ser Thr Leu Phe Pro Tyr Thr
1               5

<210> SEQ ID NO 11
<211> LENGTH: 339
<212> TYPE: DNA
<213> ORGANISM: Mus musculus

<400> SEQUENCE: 11
gaggtgcagc tggtggagtc tggtggagga ttggtgcagc ctaaagggtc attgaaactc     60
tcatgtgcag cctctggatt caccttcaat acctacgcca tgaactgggt ccgccaggct    120
ccaggaaagg gtttggaatg ggttgctctc ataagaacta aaattaataa ttattcaaca    180
tattatgccg attcagtgaa agacaggttc accatctcca gagatgattc acaaagcatg    240
ctctatctgc aaatgaacaa cttgaaaact gaggacacag gcatttatta ctgtgtgagt    300
gtttactggg gccaggggac tctggtcact gtctctgca                           339

<210> SEQ ID NO 12
<211> LENGTH: 113
<212> TYPE: PRT
<213> ORGANISM: Mus musculus

<400> SEQUENCE: 12

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Leu Ile Arg Thr Lys Ile Asn Asn Tyr Ser Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Gly Ile Tyr
                85                  90                  95

Tyr Cys Val Ser Val Tyr Trp Gly Gln Gly Thr Leu Val Thr Val Ser
            100                 105                 110

Ala

<210> SEQ ID NO 13
<211> LENGTH: 336
<212> TYPE: DNA
<213> ORGANISM: Mus musculus

<400> SEQUENCE: 13
gatattgtga tgacccaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttcct    300
ccgacgttcg gtggaggcac caagctggaa atcaaa                              336

<210> SEQ ID NO 14
<211> LENGTH: 112
<212> TYPE: PRT

-continued

<213> ORGANISM: Mus musculus

<400> SEQUENCE: 14

Asp Ile Val Met Thr Gln Ala Ala Phe Ser Asn Pro Val Thr Leu Gly
1               5                   10                  15
Thr Ser Ala Ser Ile Ser Cys Arg Ser Ser Lys Ser Leu Leu His Ser
            20                  25                  30
Asn Gly Ile Thr Tyr Leu Tyr Trp Tyr Leu Gln Lys Pro Gly Gln Ser
        35                  40                  45
Pro Gln Leu Leu Ile Tyr Gln Met Ser Asn Leu Ala Ser Gly Val Pro
    50                  55                  60
Asp Arg Phe Ser Ser Ser Gly Ser Gly Thr Asp Phe Thr Leu Arg Ile
65                  70                  75                  80
Ser Arg Val Glu Ala Glu Asp Val Gly Val Tyr Tyr Cys Ala Gln Asn
                85                  90                  95
Leu Glu Leu Pro Pro Thr Phe Gly Gly Gly Thr Lys Leu Glu Ile Lys
            100                 105                 110

<210> SEQ ID NO 15
<211> LENGTH: 10
<212> TYPE: PRT
<213> ORGANISM: Mus musculus

<400> SEQUENCE: 15

Gly Phe Thr Phe Asn Thr Tyr Ala Met Asn
1               5                   10

<210> SEQ ID NO 16
<211> LENGTH: 19
<212> TYPE: PRT
<213> ORGANISM: Mus musculus

<400> SEQUENCE: 16

Leu Ile Arg Thr Lys Ile Asn Asn Tyr Ser Thr Tyr Tyr Ala Asp Ser
1               5                   10                  15
Val Lys Asp

<210> SEQ ID NO 17
<211> LENGTH: 2
<212> TYPE: PRT
<213> ORGANISM: Mus musculus

<400> SEQUENCE: 17

Val Tyr
1

<210> SEQ ID NO 18
<211> LENGTH: 16
<212> TYPE: PRT
<213> ORGANISM: Mus musculus

<400> SEQUENCE: 18

Arg Ser Ser Lys Ser Leu Leu His Ser Asn Gly Ile Thr Tyr Leu Tyr
1               5                   10                  15

<210> SEQ ID NO 19
<211> LENGTH: 7
<212> TYPE: PRT
<213> ORGANISM: Mus musculus

<400> SEQUENCE: 19

Gln Met Ser Asn Leu Ala Ser
1               5

<210> SEQ ID NO 20
<211> LENGTH: 9
<212> TYPE: PRT
<213> ORGANISM: Mus musculus

<400> SEQUENCE: 20

Ala Gln Asn Leu Glu Leu Pro Pro Thr
1               5

<210> SEQ ID NO 21
<211> LENGTH: 339
<212> TYPE: DNA
<213> ORGANISM: Mus musculus

<400> SEQUENCE: 21

```
caggtccaac tgcagcagcc tgggtctgag ctggtgaggc ctggagcttc agtgaagctg    60
tcctgcaagg cttctggcta cacattcacc aactactgga tgcactgggt gaagcagagg   120
catggacaag ccttgagtg gattggaaat atttatcctg gcagtgttag tactaactac   180
gatgagaagt tcaagaacaa ggccacactg actgtagaca catcctccaa cacagcctac   240
atggacctca gcagcctgac atctgaggat tctgcggtct attactgtac aagatccttc   300
tatgactggg gccaaggac tctggtcact gtctctgca                          339
```

<210> SEQ ID NO 22
<211> LENGTH: 113
<212> TYPE: PRT
<213> ORGANISM: Mus musculus

<400> SEQUENCE: 22

Gln Val Gln Leu Gln Gln Pro Gly Ser Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg His Gly Gln Gly Leu Glu Trp Ile
        35                  40                  45

Gly Asn Ile Tyr Pro Gly Ser Val Ser Thr Asn Tyr Asp Glu Lys Phe
    50                  55                  60

Lys Asn Lys Ala Thr Leu Thr Val Asp Thr Ser Ser Asn Thr Ala Tyr
65                  70                  75                  80

Met Asp Leu Ser Ser Leu Thr Ser Glu Asp Ser Ala Val Tyr Tyr Cys
                85                  90                  95

Thr Arg Ser Phe Tyr Asp Trp Gly Gln Gly Thr Leu Val Thr Val Ser
            100                 105                 110

Ala

<210> SEQ ID NO 23
<211> LENGTH: 336
<212> TYPE: DNA
<213> ORGANISM: Mus musculus

<400> SEQUENCE: 23

```
gatgttgtgg tgacccaaag tccactctcc ctgcctgtca gtcttggaga tcaagcctcc    60
atctcttgca gatctagtca gagccttta cacattaatg agacaccta tttacactgg   120
ttcctgcaga agccaggcca gtctccaaaa ctcctgatct acaaactttc cacccgattt   180
```

```
tctggggtcc cagacaggtt cagtggcagt ggatcaggga cagatttcac actcaagatc    240
agcagagtgg aggctgaaga tatgggaatt tatttctgct ctcaaagtac tcatgttcct    300
ttcacgttcg gtgctgggac caagctggaa ctgaga                              336
```

```
<210> SEQ ID NO 24
<211> LENGTH: 112
<212> TYPE: PRT
<213> ORGANISM: Mus musculus

<400> SEQUENCE: 24
```

Asp Val Val Val Thr Gln Ser Pro Leu Ser Leu Pro Val Ser Leu Gly
1               5                   10                  15

Asp Gln Ala Ser Ile Ser Cys Arg Ser Ser Gln Ser Leu Leu His Ile
            20                  25                  30

Asn Gly Asp Thr Tyr Leu His Trp Phe Leu Gln Lys Pro Gly Gln Ser
        35                  40                  45

Pro Lys Leu Leu Ile Tyr Lys Leu Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Ile Tyr Phe Cys Ser Gln Ser
                85                  90                  95

Thr His Val Pro Phe Thr Phe Gly Ala Gly Thr Lys Leu Glu Leu Arg
            100                 105                 110

```
<210> SEQ ID NO 25
<211> LENGTH: 10
<212> TYPE: PRT
<213> ORGANISM: Mus musculus

<400> SEQUENCE: 25
```

Gly Tyr Thr Phe Thr Asn Tyr Trp Met His
1               5                   10

```
<210> SEQ ID NO 26
<211> LENGTH: 17
<212> TYPE: PRT
<213> ORGANISM: Mus musculus

<400> SEQUENCE: 26
```

Asn Ile Tyr Pro Gly Ser Val Ser Thr Asn Tyr Asp Glu Lys Phe Lys
1               5                   10                  15

Asn

```
<210> SEQ ID NO 27
<211> LENGTH: 4
<212> TYPE: PRT
<213> ORGANISM: Mus musculus

<400> SEQUENCE: 27
```

Ser Phe Tyr Asp
1

```
<210> SEQ ID NO 28
<211> LENGTH: 16
<212> TYPE: PRT
<213> ORGANISM: Mus musculus

<400> SEQUENCE: 28
```

Arg Ser Ser Gln Ser Leu Leu His Ile Asn Gly Asp Thr Tyr Leu His

```
1               5               10              15
```

<210> SEQ ID NO 29
<211> LENGTH: 7
<212> TYPE: PRT
<213> ORGANISM: Mus musculus

<400> SEQUENCE: 29

Lys Leu Ser Thr Arg Phe Ser
1               5

<210> SEQ ID NO 30
<211> LENGTH: 9
<212> TYPE: PRT
<213> ORGANISM: Mus musculus

<400> SEQUENCE: 30

Ser Gln Ser Thr His Val Pro Phe Thr
1               5

METHOD OF DETECTING HEART FAILURE, DEVICE FOR DETECTING HEART FAILURE, SANDWICH IMMUNOASSAY METHOD, AND COMBINATION OF ANTIBODIES

TECHNICAL FIELD

An embodiment of the present invention relates to a method of detecting heart failure, a device for detecting heart failure, and a sandwich immunoassay method, in which used are a first antibody for capturing, for which an epitope lies on any site among positions 31 to 67 of the amino acid sequence of NT-proANP and a second antibody for labeling, for which an epitope lies on any site among positions 31 to 67 of the amino acid sequence of NT-proANP; and also relates to a combination of these antibodies, and others.

BACKGROUND ART

Heart failure represents a pathological condition in which the blood outflow from the heart is insufficient, and the circulation volume cannot be maintained enough for satisfying systemic demands. Many heart-affecting diseases may be responsible for heart failure, for example, congenital heart diseases, valvular diseases (for example, mitral incompetence, tricuspid valve insufficiency, aortic incompetence, pulmonic insufficiency, and the like), myocardial diseases (for example, dilated cardiomyopathy, hypertrophic cardiomyopathy, myocarditis, and the like), filariasis, vascular diseases (for example, thrombosis, embolism, arteriosclerosis, and the like), hypertension, and the like.

Heart failure often shows almost no significant symptoms in the early pathological stage, and then gradually manifests its symptoms such as short breath and fatigue over a period of days or in some cases of years. Symptoms of heart failure may remain stable fora long time, but often progress slowly without being noticed. Early detection of heart failure is important because heart failure is generally a progressive disease where the severity gradually increases if it is not adequately treated, and also because the prognosis is poor in many cases.

ANP (Atrial natriuretic peptide) is a physiologically active peptide consisting of 28 amino acids. ANP is secreted into blood from atrial myocytes in response to a stimulus such as increased body fluid and elevated internal pressure in the atrium. It acts as a hormone, and targets organs such as kidney and blood vessel, and has strong natriuretic, angiectatic, and hypotensive activities. However, it has a half-life in blood of about 100 seconds, which is difficult to be measured.

ANP is biosynthesized as its precursor proANP (Proatrial natriuretic peptide) in atrial myocytes and other places. The precursor of ANP, proANP, consists of 126 amino acids, and is composed of NT-proANP (N-terminal proANP) having an amino acid sequence of positions 1 to 98 and ANP having an amino acid sequence of positions 99 to 126. It is cleaved into NT-proANP and ANP when secreted into blood from atrial myocytes or other places.

For human, dog and other species, ANP in blood is known to be increased upon congestive heart failure and the like. Therefore, ANP is also known to be useful as a marker for heart failure and the like. However, simple and highly accurate measurement of ANP is difficult due to its poor stability and short half-life in blood as described above. Accordingly, various attempts have been made and proposed for using NT-proANP in blood as a marker for heart failure and the like in place of ANP.

For example, Patent Document 1 describes a sandwich immunoassay method and the like which use a first or second antibody recognizing positions 43 to 66 of the amino acid sequence of N peptide. Patent Document 2 describes sandwich immunoassay and the like which use a first antibody recognizing positions 53 to 72 of the amino acid sequence of NT-proANP, and a second antibody recognizing positions 73 to 90 of the amino acid sequence of NT-proANP. Patent Document 3 describes an immunoassay method and a method of detecting canine heart diseases, which use an antibody recognizing positions 31 to 40 of the amino acid sequence of canine NT-proANP, and an antibody recognizing positions 74 to 82 of the amino acid sequence of canine NT-proANP.

In addition, Nonpatent Document 1 describes that human NT-proANP was further cleaved and decomposed into 3 pieces: positions 1 to 30, positions 31 to 67, positions 79 to 98 of the amino acid sequence during circulation in blood, and that a fragment having an amino acid sequence of positions 31 to 67 of human NT-proANP showed the highest sensitivity as a marker for congestive heart failure.

CITATION LIST

Patent Document 1: Japanese Patent Application Laid-Open No. H8-226919
Patent Document 2: Japanese Translation of PCT International Application Publication No. 2006-523298
Patent Document 3: Japanese Patent Application Laid-Open No. 2014-210761
Nonpatent Document 1: Sreedevi Daggubati, James R. Parks, Rose M. Overton, Guillermo Cintron, Douglas D. Schocken, David L. Vesely, "Adrenomedullin, endothelin, neuropeptide Y, atrial, brain, and C-natriuretic prohormone peptides compared as early heart failure indicators". Cardiovascular Research (36)246-255, 1997

DISCLOSURE OF THE INVENTION

Problem to be Solved by the Invention

An object of the present invention is to detect heart failure more simply and highly accurately, and the like.

Means for Solving the Problems

The present inventors uniquely found that actually, the full-length of NT-proANP is rarely maintained in blood circulation, and is likely fragmented in the early phase. Based on the above finding, the present inventors also successfully made two types of antibodies for which epitopes lie on any site among positions 31 to 67 of the amino acid sequence of NT-proANP, the epitopes being not overlapped with each other. Further, the present inventors demonstrated that NT-proANP in a biological sample can be measured simply and highly accurately by performing sandwich immunoassay using these antibodies to detect heart failure.

Accordingly, an embodiment of the present invent provides a method of detecting heart failure using a sample collected from an organism, the method comprising performing sandwich immunoassay of NT-proANP or a fragment thereof contained in the sample using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP.

According to an embodiment of the present invention, the epitopes of the two types of antibodies: one for capturing and the other for labeling, both of which lie among positions 31 to 67 of the amino acid sequence of NT-proANP. This, therefore, enables detention of a fragment having the same amount of substance as NT-proANP before cleavage and decomposition even if NT-proANP is further cleaved and decomposed into 3 pieces: an amino acid sequence of positions 1 to 30, an amino acid sequence of positions 31 to 67, and an amino acid sequence of positions 68 to 98 during circulation in blood. Therefore, by performing sandwich immunoassay of NT-proANP or a fragment thereof using a combination of these antibodies, NT-proANP in a biological sample can be measured simply and highly accurately to detect heart failure.

The Sequence Listing named 203-Sequence-Listing-ST25-17135-KS014US, created on 11 Feb. 2025 and of 12,807 bytes in size is incorporated herein by reference.

As a sandwich immunoassay method, immunochromatography may be used, for example. More specifically, in immunochromatography, NT-proANP or a fragment thereof contained in a sample may be measured, for example, by performing (1) a step of applying the sample in the upstream side of a flow path along which a liquid develops due to capillarity and (2) a step of allowing the sample to pass through, in this order, a first region where the aforementioned second antibody labelled with a labeling substance is retained and a second region where the aforementioned first antibody is fixed on the flow path while allowing the liquid to develop from the upstream side to the downstream side along the flow path. Thereby, measurement of NT-proANP for detecting heart failure can be achieved by a simple operation of applying a sample in the upstream side of a flow path. Further, this method can be performed with a device having a relatively simple structure which can also be manufactured on a large scale relatively easily. Therefore, the method enables relatively simple and inexpensive test and detection of heart failure for a large number of individuals, leading to broad utility.

An embodiment of the present invention can be applied to detection of heart failure not only for mammal including human but also for nonhuman mammal, for example, dog or cat. For example, dog or cat may suffer severe and relatively frequent heart diseases such as mitral incompetence, cardiomyopathy, filariasis. For detecting these diseases in their early stages, early detection of heart disease is highly desired. Individuals of nonhuman mammal themselves, however, cannot complain their poor conditions, and faint signs of heart failure need to be found by owner's observation, periodic diagnosis, and the like. Consequently, early detection is often very difficult as compared with that for human. In contrast, an embodiment of the present invention can detect heart failure highly accurately by a simple procedure of only performing sandwich immunoassay on samples obtained from these individuals, leading to broad utility particularly in detection of heart failure for nonhuman mammal.

Advantageous Effects of Invention

An embodiment of the present invention enables simple and highly accurate detection of heart failure.

DETAILED DESCRIPTION

<Combination of Antibodies According to an Embodiment of the Present Invention>

An embodiment of the present invention encompasses all combinations of two types of antibodies: one for capturing and the other for labeling for use in sandwich immunoassay, in which epitopes for both of the antibodies reside on any site among positions 31 to 67 of the amino acid sequence of NT-proANP, and the epitopes do not overlap with each other.

SEQ ID NO: 1 represents an example of the amino acid sequence of canine proANP, in which positions 1 to 98 correspond to NT-proANP, and positions 99 to 126 correspond to ANP. It is thought to be cleaved into NT-proANP and ANP by serine protease and the like when proANP is secreted into blood from atrial myocytes and other places.

NT-proANP (positions 1 to 98 of the sequence of SEQ ID NO: 1) further has cleavage sites between positions 30 and 31 and between positions 67 and 68 for aspartic protease and serine protease, respectively. Human NT-proANP is thought to be further cleaved into 3 pieces: an amino acid sequence of positions 1 to 30, an amino acid sequence of positions 31 to 67, and an amino acid sequence of positions 68 to 98.

The sandwich immunoassay according to an embodiment of the present invention uses a first antibody for capturing and a second antibody for labeling for which epitopes lie on any site among positions 31 to 67 of the amino acid sequence of NT-proANP, and the epitopes do not overlap with each other. Epitopes for the two types of antibodies do not overlap with each other, and thus the antibodies can be bound respectively to a separate region of positions 31 to 67 of the amino acid sequence of NT-proANP or a fragment including that portion, allowing simultaneous binding without competition. Therefore, a combination of an antibody for capturing and an antibody for labeling can be applied to sandwich immunoassay. Further, use of the antibodies, both of which can be bound to any site among positions 31 to 67 of the amino acid sequence of NT-proANP, can detect the same amount of substance as NT-proANP originally present before cleavage and decomposition not only when the full-length of NT-proANP is maintained at the time of measurement but also when NT-proANP is already cleaved between positions 30 and 31 and/or between positions 67 and 68 before measurement. Therefore, by performing sandwich immunoassay of NT-proANP using a combination of these antibodies, NT-proANP in a biological sample can be measured simply and highly accurately to detect heart failure.

The above two types of antibodies may be a combination of antibodies which can recognize any site among positions 31 to 67 of the amino acid sequence of NT-proANP from animal species for which heart failure is to be detected, the antibodies having recognition regions not overlapping with each other. The present invention shall not be limited narrowly to any specific amino acid sequences of NT-proANP from any specific animal species, nor to any specific recognition regions residing amino positions 31 to 67 of the amino acid sequence of NT-proANP. Further, the present invention shall not only be limited to monoclonal antibody although it is preferred.

Depending on animal species for which heart failure is to be detected, an antibody which can recognize any region among positions 31 to 67 of the amino acid sequence of NT-proANP from that animal species, that is, an antibody which is directed to an epitope residing on any site among positions 31 to 67 of any amino acid sequence of NT-proANP from that animal species, for example, may be used.

For example, in order to detect heart failure of human, dog, or cat, an antibody is generated based on the amino acid sequence of human NT-proANP, canine NT-proANP, or feline NT-proANP, respectively. It is noted that when epitopes for both of a pair of antibodies are common in sequence between animal species, these antibodies can even recognize any region among positions 31 to 67 of the amino acid of NT-proANP from different animal species than the original animal species. Therefore, it is possible to detect heart failure of two or more animal species using the same combination of antibodies. For example, a pair of antibodies which can recognize any region among positions 45 to 64 of the amino acid sequence of human or canine NT-proANP, that is, a pair of antibodies for which epitopes lie any region among positions 45 to 64 of the amino acid sequence of human or canine NT-proANP may be used to measure both human and canine NT-proANP with the same combination of antibodies, thereby enabling detection of heart failure because the amino acid sequence of positions 45 to 64 of NT-proANP is completely identical between human and dog.

The following combinations may be used, for example, (1) a combination of one antibody for which an epitope lies on any site among positions 45 to 54 of the amino acid sequence of NT-proANP and the other antibody for which an epitope lies on any site among positions 55 to 64 of the amino acid sequence of NT-proANP;

(2) a combination of one antibody for which an epitope lies on any site among positions 31 to 42 of the amino acid sequence of NT-proANP and the other antibody for which an epitope lies on any site among positions 55 to 64 of the amino acid sequence of NT-proANP;

or (3) a combination of one antibody for which an epitope lies on any site among positions 31 to 42 of the amino acid sequence of NT-proANP and the other antibody for which an epitope lies on any site among positions 49 to 60 of the amino acid sequence of NT-proANP or the like. In addition, for example, any one antibody in a combination of a pair of antibodies may be directed to an epitope residing on any site among positions 39 to 51 or positions 39 to 54 of the amino acid sequence of NT-proANP.

Each of the antibodies according to these combinations can be generated by a known method.

As an antigen which may be used for generating these antibodies, for example, a synthetic peptide may be used having the same amino acid sequence as any site among positions 31 to 67 of the amino acid sequence of NT-proANP from animal species for which heart failure is to be detected. For example, these antibodies may be generated by separately immunizing animal using a synthetic peptide having an amino acid sequence of any site among positions 45 to 54 of the amino acid sequence of NT-proANP and a synthetic peptide having an amino acid sequence of any site among positions 55 to 64 of the amino acid sequence of NT-proANP. For example, one of a pair of antibodies may also be generated by immunizing animal using a synthetic peptide having an amino acid sequence of any site among positions 31 to 42 of the amino acid sequence of NT-proANP, a synthetic peptide having an amino acid sequence of any site among positions 39 to 54 of the amino acid sequence of NT-proANP, or a synthetic peptide having an amino acid sequence of any site among positions 49 to 60 of the amino acid sequence of NT-proANP. These synthetic peptides can be chemically synthesized by a known method.

These synthetic peptides may each be attached to a known carrier protein such as, for example, bovine serum albumin (BSA), hemocyanin (KLH), and bovine thyroglobulin (BTG), or a synthetic polymer carrier such as polyamino acids, polystyrenes, and polyacrylates, and then used to immunize animal. A synthetic peptide may be attached to a career protein or a synthetic polymer carrier according to a known method, for example, methods using a diazonium compound, a dialdehyde compound, a dimaleimide compound, a maleimide active ester compound, a carbodiimide compound, and the like.

An antigen prepared in this way may be administered to animal for immunization. There is no particular limitation for animal to be immunized. As animal to be immunized may be, for example, monkey, rabbit, dog, guinea pig, mouse, rat, sheep, goat, or the like, and preferably may be mouse. There is no particular limitation for the dose and mode of administration of an antigen to these animals, and any known method may be used. For example, immunization may be performed a total of 2 to 10 times every 4 days to 6 weeks via intraperitoneal, intravenous, or subcutaneous administration, and the like. An appropriate amount of an appropriate adjuvant (for example, Freund's complete adjuvant, Freund's incomplete adjuvant, and the like) may be mixed with an antigen to make an emulsion before administering it to animal for immunization.

In order to produce monoclonal antibody, hybridoma, which produces that antibody, may be established. Hybridoma may be established by a known method. For example, an individual showing an elevated antibody titer may be selected from immunized animals, and the spleen or lymph gland excised from that individual 1 to 8 days after the final immunization may be fused with myeloma cells from the same animal species as the immunized animals to create a monoclonal-antibody producing hybridoma cell line. For example, P3 (P3-X63Ag8, P3U1 (P3-X63Ag8U1)), X63.653 (X63Ag8.653), SP2 (Sp2/0-Ag14), FO, NS-1 (NSI/1-Ag4-1), NSO/1, FOX-NY, and the like may be used as a mouse-derived myeloma cell line, and, for example, Y3-Ag1.2.3, YB2/0, IR983F, and the like may be used as a rat-derived myeloma cell line. For example, mouse-derived myeloma cells are suitable when mouse is immunized. Spleen cells may be fused with myeloma cells using, for example, PEG (polyethylene glycol). For example, antibody-producing cells (cells of spleen, lymph gland, and the like) collected from an immunized animal and myeloma cells are thoroughly mixed at a ratio of about 1:1 to 10:1 in a culture medium, and a PEG solution (for example, one having an average molecular weight of about 1,000 to 6,000) heated to 37° C. is added to and mixed with the both cells at about 30 to 60% (w/v) to achieve fusion of the both cells. After cell fusion, PEG is removed, and the fused cells at a predetermined concentration are seeded on a HAT selection medium (a medium containing hypoxanthine, aminopterin, thymidine) and the like, and cultured for several days to several weeks to kill non-hybridoma cells, thereby selecting hybridoma cells. Among hybridoma cells survived in the selection medium, those producing an antibody of interest are screened. There is no particular limitation for a method of screening. For example, systems such as ELISA (Enzyme-linked immunosorbent assay), flow cytometry, western blotting, dot blotting, and radioimmunoassay may be used to determine the presence or absence of binding of an antigen with an antibody present in the supernatant of hybridoma culture, thereby selecting hybridoma cell line of interest. Hybridoma cells which produce an antibody of interest are then selected, and, if desired, monocloning is performed to establish antibody-producing hybridoma cells.

For example, a hybridoma cell line established may be cultured in a known medium or under known conditions, and monoclonal antibody can be obtained from the resulting culture supernatant. Alternatively, the hybridoma cell line may be, for example, administered intraperitoneally to mouse and the like for proliferation, and highly concentrated monoclonal antibody can be obtained by collecting ascitic fluid from the mouse.

Antibody contained in a culture supernatant, an ascitic fluid, and the like may be purified by a known method. The followings may be used to purify antibody with high purity: for example, alcohol precipitation, isoelectric point precipitation, electrophoresis, adsorption and desorption methods using ion-exchange columns (for example, DEAE), ultracentrifugation, gel filtration, methods using active sorbents (Protein A, Protein G, and the like), affinity chromatography, and the like.

Any of the following established hybridoma cell lines may be used as a combination of a pair: for example, Accession Number NITE BP-02602 (Depository Organization: National Institute of Technology and Evaluation, Patent Microorganisms Depositary, 2-5-8 Kazusakamatari Kisarazu Chiba, Japan. Original deposition day: Dec. 27, 2017), Accession Number NITE BP-02603 (Depository Organization: National Institute of Technology and Evaluation, Patent Microorganisms Depositary, 2-5-8 Kazusakamatari Kisarazu Chiba, Japan. Original deposition day: Dec. 27, 2017), Accession Number NITE BP-02604 (Depository Organization: National Institute of Technology and Evaluation, Patent Microorganisms Depositary, 2-5-8 Kazusakamatari Kisarazu Chiba, Japan. Original deposition day: Dec. 27, 2017), Accession Number NITE BP-02605 (Depository Organization: National Institute of Technology and Evaluation, Patent Microorganisms Depositary, 2-5-8 Kazusakamatari Kisarazu Chiba, Japan. Original deposition day: Dec. 27, 2017), Accession Number NITE BP-02606 (Depository Organization: National Institute of Technology and Evaluation, Patent Microorganisms Depositary, 2-5-8 Kazusakamatari Kisarazu Chiba, Japan. Original deposition day: Dec. 27, 2017). The hybridoma cell line of Accession Number NITE BP-02602 produces antibody for which an epitope lies on any site among positions 31 to 42 of the amino acid sequence of canine NT-proANP. The hybridoma cell line of Accession Number NITE BP-02603 produces antibody for which an epitope lies on any site among positions 49 to 60 of the amino acid sequence of canine NT-proANP. The hybridoma cell line of Accession Number NITE BP-02604 produces antibody for which an epitope lies on any site among positions 45 to 54 of the amino acid sequence of canine NT-proANP. The hybridoma cell line of Accession Number NITE BP-02605 produces antibody for which an epitope lies on any site among positions 55 to 64 of the amino acid sequence of canine NT-proANP. The hybridoma cell line of Accession Number NITE BP-02606 produces antibody for which an epitope lies on any site among positions 55 to 64 of the amino acid sequence of canine NT-proANP. Therefore, the followings may be used as a combination of antibodies according to an embodiment of the present invention: for example, (1) an monoclonal antibody produced by the hybridoma cell line of Accession Number NITE BP-02602 and an monoclonal antibody produced by the hybridoma cell line of Accession Number NITE BP-02603; (2) an monoclonal antibody produced by the hybridoma cell line of Accession Number NITE BP-02602 and an monoclonal antibody produced by the hybridoma cell line of Accession Number NITE BP-02604; (3) an monoclonal antibody produced by the hybridoma cell line of Accession Number NITE BP-02602 and an monoclonal antibody produced by the hybridoma cell line of Accession Number NITE BP-02605 or NITE BP-02606; (4) an monoclonal antibody produced by the hybridoma cell line of Accession Number NITE BP-02604 and an monoclonal antibody produced by the hybridoma cell line of Accession Number NITE BP-02605 or NITE BP-02606, and the like.

<Sandwich Immunoassay Method According to Embodiment of the Present Invention>

The present invention encompasses all of sandwich immunoassay methods using the aforementioned combinations of antibodies, i.e., sandwich immunoassay methods using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP.

As described above, an embodiment of the present invention uses a first antibody for capturing and a second antibody for labeling for which epitopes lie on any site among positions 31 to 67 of the amino acid sequence of NT-proANP and the epitope do not overlap with each other. Therefore, in addition to full-length proANP (positions 1 to 126), full-length NT-proANP (positions 1 to 98) present in blood and the like, a fragment having an amino acid sequence of positions 31 to 98 or positions 31 to 126 (a product cleaved between positions 30 and 31), a fragment having an amino acid sequence of positions 1 to 67 (a product cleaved between positions 67 and 68), even a fragment having an amino acid sequence of positions 31 to 67 (a product cleaved between positions 30 and 31 and positions 67 to 68), and the like can be captured and detected without being passed through. That is, irrespective of whether it is cleaved or at which site it is cleaved, the amount of substance similar to that of proANP or a cleavage product thereof, NT-proANP, can theoretically be detected.

Use of the aforementioned pair of antibodies: one for capturing and the other for labeling in a sandwich immunoassay method enables simple and highly accurate capture and detection of NT-proANP or a fragment thereof. There is no particular limitation for a sandwich immunoassay method, and any known methods can be widely used. For example, the followings may be used: sandwich enzyme immunoassay (EIA) such as ELISA (Enzyme-linked immunosorbent assay); immunochromatography based on a sandwich method; sandwich radioimmunoassay (RIA); sandwich fluoroimmunoassay (FIA); sandwich chemiluminescent immunoassay (CLIA); sandwich chemiluminescent enzyme immunoassay (CLEIA); and the like.

Sandwich immunoassay by the ELISA method may be performed according to a known procedure, for example, a procedure comprising the steps of: fixing a primary antibody for capturing to a solid material; adding a sample; adding an enzyme-labelled secondary antibody; adding a solution of a substrate; and measuring absorbance. Specifically, the first antibody for capturing is first fixed to, for example, a support such as a 96-well plate; beads such as polystyrene beads; a tube; a membrane of cellulose nitrate and the like, and then washed. A blocking agent is then added, and washed. Next, a sample is added and incubated, and then washed. Next, the enzyme-labelled second antibody is added and incubated, and then washed. Next, a solution of a chromogenic substrate for the enzyme is added for a certain time of period to allow the substrate become a dye through an enzyme reaction. A quenching solution is then added to stop the enzyme reaction. After the enzyme reaction is quenched, absorbance is measured to compute the amount of an antigen in the measurement sample based on the degree of coloration of the dye. According to these steps, NT-proANP or a fragment thereof can be measured quantitatively. Enzymes which can be used as labels may include, for example, β-galactosidase (β-GAL), alkaline phosphatase (ALP), horseradish peroxidase (HRP), and the like. Chromogenic substrates which can be used may include, for example, TMB (3,3',5,5'-tetramethylbenzidine), and the like. Quenching solutions which can be used may include, for example, acids such as sulfuric acid.

Sandwich immunoassay by immunochromatography may be performed according to a known procedure, for example, a procedure comprising the steps of: applying the sample in the upstream side of a flow path along which a liquid develops due to capillarity; and allowing the sample to pass through a first region where the second antibody labelled with a labeling substance is retained and subsequently a second region where the first antibody is fixed on the flow path while allowing the liquid to develop from the upstream side to the downstream side along the flow path. A sample applied in the upstream side of the flow path on which the first antibody for capturing is fixed at a specific region will permeate and migrate along the flow path from upstream to downstream. On the way of this process, an antigen in the sample will be bound to the labelled second antibody, and the resulting antigen-antibody complex will continue to permeate and migrate further downstream. The antigen-antibody complex will be then captured by the first antibody for capturing, and will stay at that region. This enables NT-proANP or a fragment thereof to be simply and highly accurately measured in a semi-quantitative or qualitative manner based on the degree of coloring due to a labeling substance at that region. It is noted that labeling of the second antibody with a labeling substance can be performed according to a known method. Labeling substances which can be used may include, for example, latex coloring particles of organic polymers such as polystyrene and styrene-butadiene copolymers; metal colloid such as gold colloid and silver colloid; metal particles of metal sulfides and the like; and others.

Sandwich immunoassay by sandwich radioimmunoassay (RIA) may be performed according to a known procedure, for example, a procedure comprising the steps of: fixing a primary antibody for capturing to a solid material; adding a sample; adding a secondary antibody labelled with a radioactive isotope; and measuring radioactivity. Specifically, for example, beads to which a first antibody for capturing is fixed is first added to and mixed with a sample, and incubated at 25 to 37° C. for 1 to 4 hours, and then washed. Next, a solution containing a second antibody labelled with a radioactive isotope is added, and incubated at 25 to 37° C. for 1 to 4 hours, and then washed. Next, the beads are collected, and the radioactivity from an antigen-antibody complex bound to the beads is quantified with a γ-ray counter and the like. Radioactive elements which can be used as labels may include, for example, $^{14}C$, $^{3}H$, $^{32}P$, $^{125}I$, $^{131}I$, and the like. Labeling of an antibody with a radioactive isotope can be performed according to a known method, for example, the chloramine T method, the peroxidase method, the Iodogen method, the Bolton-Hunter method, and the like.

Sandwich immunoassay by sandwich fluoroimmunoassay (FIA) may be performed according to a known procedure, for example, a procedure comprising the steps of: fixing a primary antibody for capturing to a solid material; adding a sample; adding a secondary antibody labelled with a fluorescent substance; and measuring fluorescence intensity. Fluorescent substances which can be used may include, for example, fluorescein, fluorescamine, fluorescein isothiocyanate, tetramethylrhodamine isothiocyanate, and the like.

Sandwich immunoassay by sandwich chemiluminescent immunoassay (CLIA) may be performed according to a known procedure, for example, a procedure comprising the steps of: fixing a primary antibody for capturing to a solid material; adding a sample; adding a secondary antibody labelled with a luminescent substance; and measuring luminescence intensity. Luminescent substances which can be used may include, for example, luciferin, luminol, luminol derivatives, acridinium esters, and the like.

Sandwich immunoassay by sandwich chemiluminescent enzyme immunoassay (CLEIA) may be performed according to a known procedure, for example, a procedure comprising the steps of: fixing a primary antibody for capturing to antibody-associative magnetic particles; adding a sample; adding a secondary antibody labelled with a luminescent substance; magnetically collecting the resulting complex by means of magnetic force; and measuring luminescence intensity. Luminescent substances which can be used may include, for example, luciferin, luminol, luminol derivatives, acridinium esters, and the like.

<Method of Detecting Heart Failure According to Embodiment of the Present Invention>

The present invention encompasses all of the methods of detecting heart failure by performing the aforementioned sandwich immunoassay methods, i.e., methods of detecting heart failure from a sample collected from an organism, the methods comprising the step of performing sandwich immunoassay of NT-proANP or a fragment thereof contained in the sample using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP.

As described above, NT-proANP or a fragment thereof can be captured and detected simply and highly accurately by performing sandwich immunoassay of NT-proANP contained in a sample using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP, the epitope not overlapping with that for the first antibody. When a precursor of ANP, proANP is secreted into blood from atrial myocytes and other places in response to a stimulus such increased internal pressure or increased body fluid of the atrium, proANP is cleaved into NT-proANP and ANP. Therefore, NT-proANP or a fragment thereof in blood is also presumably increased by the same amount of substance when ANP in blood is increased due to congestive heart failure and the like. NT-proANP or a fragment including positions 31 to 67 of the amino acid thereof is presumably more stable and has a longer half-life than ANP. Therefore, the method according to an embodiment of the present invention can detect NT-proANP or a fragment thereof highly accurately, leading to simple and highly accurate detention of heart failure.

An embodiment of the present invention can be used to detect heart failure, i.e., a pathological condition in which the blood outflow from the heart is insufficient, and the circulatory volume cannot be maintained for satisfying systemic demands. In particular, an embodiment of the present invention is effective for early detection of a pathological condition such as congestive heart failure showing symptoms of increased internal pressure, increased body fluid of the atrium, and the like. It may also be used to detect, for example, ISACHC Classification I to II or ACVIM (American College of Veterinary Internal Medicine, the same shall apply hereinafter) Guideline Stage A to B2, i.e., subclinical to moderate atrial chronic heart failure, and the like. An embodiment of the present invention can also detect heart failure early and highly accurately. Therefore, it is also effective for detention or early detention of diseases responsible for heart failure (except for congenital heart disease), for example, valvular disease (for example, mitral incompetence, tricuspid valve insufficiency, aortic incompetence, pulmonic insufficiency, and the like), myocardial diseases (for example, dilated cardiomyopathy, hypertrophic cardiomyopathy, myocarditis, and the like), filariasis, vascular diseases (for example, thrombosis, embolism, arteriosclerosis, and the like), hypertension, and the like.

A measurement value from the aforementioned sandwich immunoassay shows a significant correlation with the progression stage of heart failure. Therefore, for example, a quantitative measurement valve obtained based on a method comprising the step of: performing the aforementioned sandwich immunoassay of NT-proANP or a fragment thereof contained in a sample using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP; and determining the progression stage of heart failure based on the resulting measurement valve.

The progression stage of heart failure may also be determined, for example, by a method comprising the steps of: pre-setting a threshold value corresponding to a progression stage of heart failure; and performing sandwich immunoassay of NT-proANP or a fragment thereof contained in a sample using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP; determining the progression stage of heart failure if the resulting measurement valve is larger than the threshold value. These enable a simple and highly accurate detection of the progression stage of heart failure in addition to detection of heart failure.

The method of detecting heart failure according to an embodiment of the present invention can also be applied to detection of heart failure not only for mammal including human but also for nonhuman mammal, for example, dog or cat. In that case as described above, sandwich immunoassay may be performed for detecting heart failure of an animal species using a pair of antibodies each of which can recognize any site among positions 31 to 67 the amino acid sequence of NT-proANP of the animal species for which heart failure is to be detected, i.e., a pair of antibodies for which epitopes lie on any site among positions 31 to 67 of the amino acid sequence of NT-proANP of that animal species. For example, a pair of antibodies may be generated based on amino acid sequences of human NT-proANP, canine NT-proANP, and feline NT-proANP to detect heart failure of human, dog, and cat, respectively.

It is noted that if epitopes for the both antibodies in a pair correspond to a sequence common between animal species, these antibodies can also recognize any site among positions 31 to 67 of the amino acid sequence of NT-proANP of an animal species different from the original animal species, and thus the same combination of antibodies can detect heart failure of two or more animal species. For example, positions 45 to 54 and positions 55 to 64 of the amino acid sequence of canine NT-proANP is completely identical to the same site of the amino acid sequence of human NT-proANP. Therefore, sandwich immunoassay performed with a combination of an antibody for which an epitope lies on any site among positions 45 to 54 of the amino acid sequence of canine NT-proANP and an antibody for which an epitope lies on any site among positions 55 to 64 of the amino acid sequence of canine NT-proANP can detect heart failure of dog and human by the identical combination of antibodies.

Those as described above may widely be used as a sandwich immunoassay method which can be used to detect heart failure. For example, when the ELISA method is used to measure NT-proANP or a fragment thereof contained in a sample, the onset, severity, or degree of risk of heart failure can be measured quantitatively. When immunochromatography is used to measure NT-proANP or a fragment thereof contained in a sample, the onset, severity, or degree of risk of heart failure can be measured quantitatively or semi-quantitively.

Samples which may be subjected to the present method of detecting heart failure (or a sandwich immunoassay method) include, for example, body fluid or excrement collected from a subject organism such as blood, serum, plasma, and urine.

<Method of Detecting Cardiac Dilatation According to Embodiment of the Present Invention>

The present invention widely encompasses the methods of detecting (a pathological condition of) cardiac dilatation which is an indicator of the progression stage of heart failure and the like, the methods comprising the steps of: performing sandwich immunoassay of NT-proANP or a fragment thereof contained in a sample using a first antibody for capturing for which an epitope lies on any site among positions 31 to 67 of the amino acid sequence of NT-proANP and a second antibody for labeling for which an epitope lies on any site among positions 31 to 67 of the amino acid sequence of NT-proANP; and determining cardiac dilatation if the resulting measurement valve is larger than a predetermined cut-off value.

A phase where cardiac dilatation is observed during the progress of heart failure corresponds to, for example, Stage B2 in accordance with the ACVIM guideline. Because an event of heart failure may occur at Stage C, making treatment difficult, it is important to start treatment of heart failure at Stage B2 even though clinical symptoms are not yet manifested. Stage B2 is also very important in view of early detection. In contrast, the sandwich immunoassay according to an embodiment of the present invention enables simple and highly accurate determination whether it is a stage where cardiac dilatation is observed by determining whether a measurement value is larger than a particular predetermined cut-off value.

A cut-off value can appropriately set, for example, depending on the binding properties or sensitivity of antibodies for used in sandwich immunoassay. For example, samples collected from a plurality of specimens having their progression stages already diagnosed may each be used to perform sandwich immunoassay, and then the resulting measurement value therefrom may be used to determine an appropriate threshold value.

<Heart-Failure Detection Device According to Embodiment of the Present Invention>

The present invention encompasses all of the devices for detecting heart failure by means of immunochromatography using the aforementioned combinations of antibodies. As a specific configuration, for example, a heart-failure detection device for detecting heart failure by an immunochromatography method comprising applying a sample collected from an organism on a flow path along which a liquid will develop through capillarity may be configured such that the flow path comprises, in this order from an upstream side, (1) a sample application portion on which the sample is to be applied, (2) a labelled-antibody retention portion for retaining a second antibody labelled with a labeling substance, (3) a measurement portion as a body portion formed with an elongated member in which a first antibody for capturing is fixed substantially linearly at a predetermined location of the elongated member in a substantially vertical direction relative to the longitudinal direction, epitopes for both of the antibodies residing on any site among positions 31 to 67 of the amino acid sequence of NT-proANP.

FIG. 1 shows a schematic perspective view of an exemplary internal structure of the heart-failure detection device according to an embodiment of the present invention. It is noted that the present invention shall not be narrowly limited only to the configuration shown in FIG. 1.

In the heart-failure detection device A of FIG. 1, arranged are a sample application portion 1 on which a sample is to be applied, a labelled-antibody retention portion 2 for retaining a second antibody labelled with a labelling substance, a measurement portion 3 as a body portion formed with an elongated member, and an absorption portion 4 for absorbing the sample developed thereto. The sample application portion 1 is contacted with the labelled-antibody retention portion 2, and the labelled-antibody retention portion 2 is contacted with the measurement portion 3 (and the measurement portion 3 is contacted with the absorption portion 4), respectively. This configuration enables a continuous flow path C to be formed along which a liquid will develop toward a downstream side C2 from an upstream side C1 due to capillarity.

The sample application portion 1 is a portion on which a sample is applied. For example, a sample may be applied on the heart-failure detection device A by dropping a sample to be measured on a substantially central region 11 on the upper surface of the sample application portion 1. In FIG. 1, at least a portion of the lower surface of the sample application portion 1 formed on a substantially rectangular plate strip is brought into surface contact with the upper surface of the labeled antibody retention portion 2 so that an applied sample will develop toward the labeled antibody retention portion 2.

There is no particular limitation for a material of the sample application portion 1 as long as an applied sample can develop toward the labelled-antibody retention portion 2, and known materials can widely be used. For example, those formed with cellulose fiber, glass fiber, polyurethane, polyacetate, cellulose acetate, nylon, and the like can be used.

The labelled-antibody retention portion 2 is a portion for retaining a second antibody labelled with a labelling substance. For example, the second antibody labelled with a labelling substance may be retained by dropping a certain amount of a solution of the labelled antibody to this portion or immersing this portion in a certain amount of a solution of the labelled antibody, and then drying. In FIG. 1, at least a portion of the upper surface of the labelled-antibody retention portion 2 formed on a substantially rectangular plate strip is brought into surface contact with the lower surface of the sample application portion 1 so that a sample applied on the sample application portion 1 will develop toward the labeled antibody retention portion 2. Further, at least a portion of the lower surface of the labelled-antibody retention portion 2 formed on a substantially rectangular plate strip is brought into surface contact with the upper surface of the measurement portion 3 so that a sample developed to the labelled-antibody retention portion 2 will continue to develop toward the measurement portion 3. During this, NT-proANP or a fragment thereof, if contained in a sample, will continue to develop toward the measurement portion 3 as a complex with the labelled second antibody.

There is no particular limitation for a material of the labelled-antibody retention portion 2 as long as a sample developed from the sample application portion 1 can further develop toward the measurement portion 3, and known materials can widely be used. For example, those formed with cellulose fiber, glass fiber, non-woven fabrics, and the like. It is noted that labeling of the second antibody with a labeling substance can be performed according to a known method as described above. Labeling substances which can be used may include, for example, latex coloring particles of organic polymers such as polystyrene and styrene-butadiene copolymers; metal colloid such as gold colloid and silver colloid; metal particles of metal sulfides and the like; and others.

The measurement portion 3 is a body portion formed with a sheet-shaped elongated member, and corresponds to a chromatography carrier. In FIG. 1, at least a portion of the upper surface of the measurement portion 3 in the upstream side is brought into surface contact with the lower surface of the labelled-antibody retention portion 2, and a sample (including a complex of NT-proANP or a fragment thereof with a labelled secondary antibody if contained in a sample) will develop from the labelled-antibody retention portion 2 to the measurement portion 3, and further continue to develop through the measurement portion 3 in the direction from the upstream side C1 to the downstream side C2.

There is no particular limitation for a material of the measurement portion 3 as long as it may be a material through which a liquid can develop due to capillarity, that is, a material which can function as a chromatography carrier, and known materials may widely be used. The followings may be used: porous carriers, for example, those formed with cellulose nitrate membrane, cellulose membrane, acetylcellulose membrane, nylon membrane, glass fiber, non-woven fabrics, and the like.

In FIG. 1, a substantially linear first-antibody fixed region 31 is formed in the substantially downstream side C2 of the middle region 32 of the measurement portion 3. In the first-antibody fixed region 31, a first antibody for capturing is fixed at a predetermined location of the elongated member as the body portion of the measurement portion 3 in an appropriately linear manner viewed from the top in a substantially vertical direction relative to the longitudinal direction. If a complex of a labelled second antibody with NT-proANP or a fragment thereof is contained in a sample which is allowed to develop through the measurement portion 3 in the direction from the upstream side C1 to the downstream side C2, the complex is captured at the first-antibody fixed region 31, and a labeling substance accumulates at this region. Then, the first-antibody fixed region 31 is colored to visualize the presence of an antigen if NT-proANP or a fragment thereof is contained in the sample. The presence or absence of coloring or the degree of coloring can be measured to determine whether NT-proANP or a fragment thereof is contained in a sample. This enables detection of heart failure.

The absorption portion 4 is a site in which a sample developed to the downstream C2 of the measurement portion 3 through the sample application portion 1 and the labelled-antibody retention portion 2 is collected via absorption. As a material of the absorption portion 4, highly absorbable materials such as filter paper, and the like may be used.

In the present device A as described above, a complex of NT-proANP or a fragment thereof with a labelled second antibody is formed at the labelled antibody retention portion 2 as a sample continues to develop from the sample application portion 1 to the absorption portion 4 along the flow path C in the direction from the upstream side C1 toward the downstream side C2. When the complex is captured at the first-antibody fixed region 31 of the measurement portion 3, that region is colored with a labeling substance. The presence or absence of coloring or the degree of coloring can be measured qualitatively or semi-quantitatively to determine whether NT-proANP or a fragment thereof is contained in a sample. Based on this result, the onset, severity, or degree of risk of heart failure can be determined.

Example 1

In Example 1, attempts were made for generating monoclonal antibodies which can bind to any site among positions 31 to 67 of the amino acid sequence of canine NT-proANP.

Two types of synthetic peptides were prepared: a synthetic peptide having cysteine added to the C-terminal side of a sequence of positions 32 to 67 of the amino acid sequence of canine NT-proANP and a synthetic peptide similarly having cysteine added to the N-terminal side of positions 31 to 66 of the amino acid sequence of canine NT-proANP. Then, KLH was attached to the former synthetic peptide and the latter synthetic peptide at the C-terminal side and the N-terminal side, respectively. A maleimide-based reagent was used to attach KLH to each synthetic peptide.

The two types of KLH-conjured peptide as antigens was each administered to mice for immunization. To mice (Balb/c, female, 7-week old, Charles River Laboratories Japan, Inc.), the KLH-conjugated peptides were each administered intraperitoneally at a dose of 100 μg for the first time and 50 μg for the second time and thereafter every 2 weeks for a total of 5 times. After 9 weeks of the final administration, 126 μg and 60 μg for boosting immunization were further administered intraperitoneally and via tail vein, respectively. They were administered as a mixture with the Freund's complete adjuvant for the first immunization, as a mixture with the Freund's incomplete adjuvant for the second to 5th immunization, and as a mixture with D's PBS (−) for boosting immunization.

The spleen was excised from each of the immunized mice 3 days after the final immunization, and the spleen cells therefrom ($6.27 \times 10^8$ cells) were fused with myeloma cells (P3U1 cell line; $6.27 \times 10^7$ cells) using 50% polyethylene glycol (from Merck), and cultured in a HAT selection medium for selection.

Screening for hybridoma cell lines which produce an antibody which can bind to canine NT-proANP was performed by the ELISA method 10 days after cell fusion. A dry plate having goat anti-mouse IgG antibody fixed on the bottom of each well was prepared, and washed 3 times with PBS containing 0.05% Tween 20 (hereinafter, referred to as "PBST"), and then 200 μL of 25% Block Ace solution (from DS Pharma Biomedical Co., Ltd.) was added to each well, and allowed to stand at room temperature for 1 hour to perform blocking. Next, after washed 3 times with PBST, 50 μL of the culture supernatant from each hybridoma cell line was added to each well. Then, 50 μL of a peptide having lysine-biotin attached to the C-terminal side of a synthetic peptide corresponding to positions 31 to 67 of canine NT-proANP prepared in 0.1% BSA containing D's PBS (−) was added to each well, and allowed to react at room temperature for 3 hours. Subsequently, after washed 4 times with 0.05% Tween 20-containing physiological saline, 100 μL of a solution of streptavidin-HRP conjugate was added to each well, and allowed to react at room temperature for 2 hours, and further washed 4 time. Then 100 μL of OPD (from SIGMA) was added to each well, and allowed to react at room temperature for 30 minutes to facilitate an enzyme reaction. Then 100 μL of 1 M sulfuric acid solution was added to quench the reaction. Absorbance at a main wavelength of 490 nm was measured for each well with a plate reader.

Hybridoma cell lines showing positive results in the screening were cloned by the limiting dilution method, and a total of 11 single-clone hybridoma cell lines which produced antibodies capable of binding to canine NT-proANP were established. The subclasses of the resulting antibodies in the culture supernatants of these cell lines were investigated using a mouse monoclonal antibody isotyping kit (from Roche). The results showed that they were IgG1 (κ) or IgG2b (κ).

A plurality of synthetic peptides having 10 to 15 amino acids in length were prepared which have any portion among positions 31 to 67 of the amino acid sequence of canine NT-proANP. These peptides each prepared in a buffer solution of sodium carbonate-sodium hydrogen carbonate (pH 9.6) in an amount of 100 μL were added to a 96-well plate at each well, and allowed to stand at the room temperature for 5 hours for fixation to the bottom. After washed twice with a PBS liquid, they were allowed to stand overnight at 4° C. in a 2% BSA solution for blocking. After washed twice with a PBS liquid, 100 μL of a culture supernatant was added to each well, and allowed to stand at room temperature for 2 hours. After washed 3 times with PBST and twice with PBS for a total of 5 times, 100 μL of AP-labelled goat anti-mouse IgG antibody prepared in a 0.5% BSA liquid was added to each well, and allowed to stand at room temperature for 1 hour. After washed 3 times with PBST and twice with PBS for a total of 5 times, 100 μL of a pNPP reagent solution was added, and then absorbance at 405 nm was continuously measured for 15 to 60 minutes at room temperature to perform epitope mapping of an antibody produced from each hybridoma. Results showed that the resulting hybridoma cell lines produced an antibody for which an epitope lies on any site among positions 45 to 54 of the amino acid sequence of canine NT-proANP, an antibody for which an epitope lies on any site among positions 49 to 60 of the amino acid sequence of canine NT-proANP, an antibody for which an epitope lies on any site among positions 55 to 64 of the amino acid sequence of canine NT-proANP, an antibody for which an epitope lies on any site among positions 31 to 42 of the amino acid sequence of canine NT-proANP, an antibody for which an epitope lies on any site among positions 45 to 54 of the amino acid sequence of canine NT-proANP, an antibody for which an epitope lies on any site among positions 39 to 51 or positions 39 to 54 of the amino acid sequence of canine NT-proANP.

Among these hybridoma cell lines, a cell line which produces an IgG2b (κ) antibody for which an epitope lies on any site among positions 31 to 42 of the amino acid sequence of canine NT-proANP was designated as "KS1

Clone 3B3-31," and internationally deposited (Accession Number NITE BP-02602). A cell line which produces an IgG2b (κ) antibody for which an epitope lies on any site among positions 49 to 60 of the amino acid sequence of canine NT-proANP was designated as "KS1 Clone 19B7-31", and internationally deposited (Accession Number NITE BP-02603). A cell line which produces an IgG1 (κ) antibody for which an epitope lies on any site among positions 45 to 54 of the amino acid sequence of canine NT-proANP was designated as "KS1 Clone 20C-13", and internationally deposited (Accession Number NITE BP-02604). A cell line which produces an IgG1 (κ) antibody for which an epitope lies on any site among positions 55 to 64 of the amino acid sequence of canine NT-proANP was designated as "KS2 Clone 1C12-5", and internationally deposited (Accession Number NITE BP-02605). Another cell line which produces an IgG1 (κ) antibody for which an epitope lies on any site among positions 55 to 64 of the amino acid sequence of canine NT-proANP was designated as "KS2 Clone No. 31-4", and internationally deposited (Accession Number NITE BP-02606).

Example 2

In Example 2, sandwich immunoassay of NT-proANP was performed using antibodies produced by the hybridoma cell lines established in Example 1 to examine their reactivity and specificity.

To each well of a 96-well plates (from Nunc), 100 µL of an antibody produced from the KS1 Clone 20 C-13 cell line (Accession Number NITE BP-02604) established in Example 1 (an antibody for which an epitope lies on any site among positions 45 to 54 of the amino acid sequence of canine NT-proANP) as a primary antibody was added, and allowed to stand overnight at room temperature for fixation to the bottom. After washed 3 times with 300 µL of PBST, 300 µL of a PBS solution with 1 to 3% BSA was added, and allowed to stand at room temperature for 2 hours to perform blocking.

Next, 4 types of peptides: full-length NT-proANP having a His tag attached to the N-terminal side (recombinant), a synthetic peptide having a sequence of positions 1 to 30 of the amino acid sequence of canine NT-proANP, a synthetic peptide having a sequence of positions 31 to 67 of the amino acid sequence of canine NT-proANP, and a synthetic peptide having a sequence of positions 68 to 98 of the amino acid sequence of canine NT-proANP were prepared as evaluation antigens. To each well, 100 µL of solutions of each peptide appropriately prepared at 0 pg/mL, 50 pg/mL, 100 pg/mL, 250 pg/mL, 500 pg/mL, 1,000 pg/mL, 2,500 pg/mL, 5,000 pg/mL, and so on were each added, and allowed to stand at 37° C. for 2 hours, and then washed 3 times with 300 µL of PBST.

Next, an antibody produced from the KS2 Clone No. 31-4 cell line (Accession Number NITE BP-02606) established in Example (an antibody for which an epitope lies on any site among positions 55 to 64 of the amino acid sequence of canine NT-proANP) was biotinylated, and 100 µL was added to each well as a secondary antibody, and allowed to stand at 37° C. for 1 hour, and then washed 3 to 5 times with 300 µL of PBST.

Next, streptavidin-HRP (from R&D) was diluted at 1/200, and 100 µL was added to each well, and allowed to stand at 37° C. for 1 hour, and then washed 3 to 5 times with 300 µL of PBST. Subsequently 100 µL of TMB (3,3',5,5'-tetramethylbenzidine; from KEM EN TEC) was added to each well, and allowed to stand at 37° C. for 20 minutes to facilitate an enzyme reaction, and then 50 µL of a 1 N solution of sulfuric acid was added to quench the reaction. Absorbance at a main wavelength of 450 nm was then measured for each well with a plate reader.

The results are shown in FIG. 2. FIG. 2 is a graph illustrating the results from sandwich ELISA using antibodies produced from hybridoma established in Example 1. In the graph, the horizontal axis represents the concentrations of an antigen added for evaluation, and the vertical axis represents OD values. In the graph, the broken line labelled as "NT-proANP" represents results from experiments where various concentrations of full-length NT-proANP was added as an evaluation antigen. The broken line labelled as "Fragment 1" represents results from experiments where various concentrations of a synthetic peptide having a sequence of positions 1 to 30 of the amino acid sequence of canine NT-proANP was added as an evaluation antigen. The broken line labelled as "Fragment 2" represents results from experiments where various concentrations of a synthetic peptide having a sequence of positions 31 to 67 of the amino acid sequence of canine NT-proANP was added. The broken line labelled as "Fragment 3" represents results from experiments where various concentrations of a synthetic peptide having a sequence of positions 68 to 98 of the amino acid sequence of canine NT-proANP was added.

As indicated in FIG. 2, the results from sandwich ELISA performed using a pair of antibodies produced from hybridoma established in Example 1 showed that a synthetic peptide (Fragment 1) having a sequence of positions 1 to 30 of the amino acid sequence of canine NT-proANP and a synthetic peptide (Fragment 3) having a sequence of positions 68 to 98 of the amino acid sequence of canine NT-proANP were not detected while full-length canine NT-proANP and a synthetic peptide having a sequence of positions 31 to 67 of the amino acid sequence of canine NT-proANP were detected in a peptide concentration-dependent manner. Further, considering the molecular weights of full-length canine NT-proANP (10,466.5) and a peptide having a sequence of positions 31 to 67 of the amino acid sequence of canine NT-proANP (3,815.2), the amount of substance of full-length NT-proANP and the fragment of positions 31 to 67 of NT-proANP detected by the sandwich ELISA were estimated to be almost equal.

These results demonstrated that sandwich ELISA using a pair of antibodies produced from hybridoma established in Example 1 can detect full-length canine NT-proANP or a fragment thereof corresponding to positions 31 to 67 highly accurately and highly specifically.

Example 3

In Example 3, attempts were made for detecting heart failure by sandwich immunoassay using antibodies produced from hybridoma cell lines established in Example 1.

Blood was collected from 50 healthy field dogs with no signs of heart failure after auscultation, and plasma from the obtained blood was appropriately diluted with a PBS solution containing 1% BSA, and used as a sample of an evaluation antigen to perform sandwich ELISA for quantifying NT-proANP or a fragment thereof as in Example 2. Full-length NT-proANP having a His tag attached to the N-terminal side in Example 2 at various concentrations was added as an evaluation antigen, and measured simultaneously to create a calibration curve.

Results showed that the blood concentration of NT-proANP or a fragment thereof of 50 healthy field dogs was, on average, 4 ng/mL.

Meanwhile, blood was collected from 4 dogs with suspected ISACHC classification II heart failure as in the healthy dogs, and plasma from the obtained blood was appropriately diluted with a PBS solution (pH 5.5) containing 1% BSA, and used as a sample of an evaluation antigen to perform sandwich ELISA for quantifying NT-proANP or a fragment thereof as in Example 2. It is noted that the following signs were observed for each dog participating in this study: (1) contracepted female, weight 4.35 kg, ISACHC classification II, heart murmur, left: Levine classification IV/systolic murmur/regurgitation; right: Levine classification II/systolic murmur/regurgitation, signs of mitral myxomatous degeneration/faint, (2) female, weight 23.3 kg, ISACHC classification II, heart murmur, left: Levine classification IV/systolic murmur/regurgitation; right: Levine classification III/systolic murmur/regurgitation, signs of tricuspid valve dysplasia/pulmonary hypertension/pulmonary stenosis, (3) female, weight 6.45 kg, ISACHC classification II, heart murmur, Levine classification VI, mitral myxomatous degeneration/tricuspid regurgitation, (4) contracepted male, weight 3.15 kg, ISACHC classification II, heart murmur, left: Levine classification VI/systolic murmur/regurgitation, right: Levine classification V/systolic murmur/regurgitation, signs of mitral myxomatous degeneration.

Results showed that the blood concentrations of NT-proANP of 4 dogs with suspected heart failure were, on average, 27.9 ng/mL, 12.0 ng/mL, 13.8 ng/mL, and 17.1 ng/mL, which were significantly higher as compared with those of the healthy field dogs (the mean was 4 ng/mL).

Example 4

In Example 4, attempts were made for detecting heart failure by sandwich immunoassay from feline specimens.

Blood was collected from 15 healthy cats with no signs of heart failure after auscultation, and plasma from the obtained blood was appropriately diluted with a PBS solution (pH 5.5) containing 1% BSA, and used as a sample of an evaluation antigen to perform sandwich ELISA for quantifying NT-proANP or a fragment thereof as in Example 3. It is noted that an antibody produced from the KS1 Clone 19B7-31 cell line (Accession Number "BP-02603") established in Example 1 and an antibody produced from the KS1 Clone 3B3-31 (Accession Number BP-02602) were used as a primary antibody (solid-phased antibody) and a secondary antibody (labelled antibody), respectively.

Results showed that the blood concentrations of NT-proANP or a fragment thereof of 15 healthy cats were 980, 694, 1,883, 2,730, 915, 1,970, 1,624, 1,650, 3,125, 915, 946, 447, 367, 6,278, and 4,656 pg/mL, and the mean was 1,945 pg/mL. These results demonstrated that this detection system can also be used for measurement in cats.

Next, blood was collected from 2 cats with suspected heart failure as in the healthy cats, and plasma from the obtained blood was appropriately diluted with a PBS solution (pH 5.5) containing 1% BSA, and used as a sample of an evaluation antigen to perform sandwich ELISA for quantifying NT-proANP or a fragment thereof. It is noted that the following signs were observed for each cat. (1) Hybrid, estimated 14 years old, contracepted male, weight 3.7 kg, signs of pulmonary stenosis, tricuspid valve dysplasia. Treatment is required. (2) Hybrid, 12 year and 7-month-old, contracepted female, 3.95 kg, signs of hyperregulatory zonal cardiomyopathy. Treatment is required.

Results showed that the blood concentrations of NT-proANP or a fragment thereof of the two cats affected by heart disease were, on average, 23,097 pg/mL and 15,355 pg/mL, which were significantly higher as compared with those of the healthy cats. These results suggested that both of the antibodies used in this experiment had a cross activity with feline NT-proANP, and this measurement system was able to detect heart failure in cats.

Example 5

In Example 5, applicability of the sandwich immunoassay according to an embodiment of the present invention to human specimens was studied.

Blood was collected from a human subject (Japanese, 56 years old, female, healthy, no medication), and plasma from the obtained blood was appropriately diluted with a PBS solution (pH 5.5) containing 1% BSA, and used to perform sandwich ELISA for measuring the concentration of NT-proANP or a fragment thereof in accordance with procedures similar to those in Example 3. A synthetic peptide of a fragment of NT-proANP (positions 31 to 76 of the amino acid sequence) was added at various concentrations as an evaluation antigen, and measured simultaneously to create a calibration curve.

Results showed that the blood concentration of NT-proANP or a fragment thereof was 6.11 ng/mL. These results suggested that this measurement system can also be applied to human.

Example 6

In Example 6, a correlation between measurement value from the sandwich immunoassay according to an embodiment of the present invention and the progression stage of heart failure was investigated as well as a cut-off value for determining the progression stage of heart failure.

In accordance with the ACVIM guideline, blood was collected from a total of 122 dogs diagnosed as Stage A1 (40 dogs), Stage B1 (22 dogs), Stage B2 (37 dogs), Stage C (15 dogs), and Stage D (8 dogs), and plasma from the obtained blood was appropriately diluted with a PBS solution (pH 5.5) containing 1% BSA, and each used as a sample of an evaluation antigen to perform sandwich ELISA for measuring the concentration of NT-proANP or a fragment thereof using procedures similar to those in Example 5.

The results are shown in FIG. 3. FIG. 3 is a graph illustrating the correlations of the progression stage of heart failure and measurement values from sandwich immunoassay. In the graph, the horizontal axis represents the stages of heart failure based on ACVIM, and the vertical axis represents the concentrations of NT-proANP in the blood samples collected from specimens diagnosed as respective stages. In the graph, the values of the concentrations of NT-proANP at each stage were shown as five-number summary, in which whiskers of the lower end and the upper end represent the minimum value and the maximum value, respectively, and a box represents the first quartile and the third quartile, and a crossbar in a box represents a median. Circular symbols in the figure represent values rejected by the null hypothesis test.

As shown in FIG. 3, measurement values of NT-proANP were increased as the stage of heart failure increased. These results confirmed that measurement values from the sandwich immunoassay according to an embodiment of the present invention were correlated with the progression stages of heart failure. These results further indicated that this measurement system can be used for quantitative or semi-quantitative measurements.

Subsequently, a cut-off value for determining a pathological condition higher than Stage B1 of the ACVIM guideline to be positive (detention of heart failure) was studied. An arbitrary value of the concentration of NT-proANP was selected as a threshold value, and the threshold value was varied. For each of selected threshold values, positive or negative was determined based on whether measurement values of NT-proANP from all of the 122 cases were higher than the threshold value. Further, the results were compared with the actual diagnosis in accordance with the ACVIM guideline to obtain data for checking whether the determination was correct or not. Next, for all of the 122 cases, the rate of correct positive determination was considered as "sensitivity," and the rate of correct negative determination was considered as specificity. Then, an ROC curve was plotted with a horizontal axis of specificity and a vertical axis of sensitivity. Finally, a threshold value which gave the maximum value in accordance with the Youden Index method was computed as the optimal cut-off value. As a result, the optimal cut-off value for determining a pathological condition higher than Stage B1 of the ACVIM guideline to be positive (detection of heart failure) was computed to be 6,281 pg/mL (sensitivity: 80.5%, specificity: 82.5%, positive predictive rate: 90.3%, negative predictive rate: 67.6%).

These results suggested that when a measurement value of NT-proANP in canine blood was, for example, 6,000 pg/mL or more, this measurement system was able to detect a pathological condition of heart failure higher than Stage B1 of the ACVIM guideline simply and highly accurately at a very early stage where no clinical symptoms were yet developed. Based on this finding, a value of 6,000 pg/mL or more may be selected as a cut-off value for determining Stage B1 or higher of the ACVIM guideline by using the present measurement system. For example, the cut-off value may suitably be a value of 6,000 to 6,500 pg/mL, more suitably a value of 6,100 to 6,400 pg/mL, and most suitably a value of 6,200 to 6,300 pg/mL.

Next, investigated was a cut-off value for determining a pathological condition higher than Stage B2 of the ACVIM guideline (specifically, a case where VHS (Vetebral Heart Size) in a chest X-ray examination was larger than 10.2 or a case where the LA/Ao ratio in a cardiac echo examination was 1.6 or more) to be positive (detection of heart failure). An arbitrary value of the concentration of NT-proANP was selected as a threshold value as in the above, and the threshold value was varied. For each of the selected threshold values, positive or negative was determined based on whether measurement values of NT-proANP from all of the 122 cases were higher than the threshold value. Further, the results were compared with the actual diagnosis in accordance with the ACVIM guideline to obtain data for checking whether the determination was correct or not. Next, for all of the 122 cases, the rate of correct positive determination was considered as "sensitivity," and the rate of correct negative determination was considered as specificity. A ROC curve was plotted with a horizontal axis of specificity and a vertical axis of sensitivity. Finally, a threshold value which gave the maximum value in accordance with the Youden Index method was computed as the optimal cut-off value. As a result, the optimal cut-off value for determining a pathological condition higher than Stage B2 of the ACVIM guideline to be positive (detection of heart failure) was computed to be 8,498 μg/mL (sensitivity: 83.7%, specificity: 78.4%, positive predictive rate: 67.6%, negative predictive rate: 89.9%).

These results suggested that when a measurement value of NT-proANP in canine blood was, for example, 8,000 pg/mL or more, this measurement system was able to detect a pathological condition of heart failure higher than Stage B2 of the ACVIM guideline simply and highly accurately at a very early stage where no clinical symptoms were yet developed. Based on this finding, a value of 8,000 pg/mL or more may be selected as a cut-off value for determining Stage B2 or higher of the ACVIM guideline by using the present measurement system. For example, the cut-off value may suitably be a value of 8,000 to 9,000 pg/mL, more suitably a value of 8,200 to 8,800 pg/mL, and most suitably a value of 8,400 to 8,600 pg/mL.

It is noted that diagnosing heart failure or determining when treatment should be started is often performed based on whether or not it reaches this stage. Therefore, this measurement means according to an embodiment of the present invention is highly useful for dogs in terms of determining whether the pathological condition is higher than Stage B2 of the ACVIM guideline simply and highly accurately.

BRIEF DESCRIPTION OF THE DRAWINGS

FIG. 3 is a graph illustrating the correlations of the progression stages of heart failure and measurement values from sandwich immunoassay in Example 6.

DESCRIPTION OF THE REFERENCE NUMERALS

Figure 1:
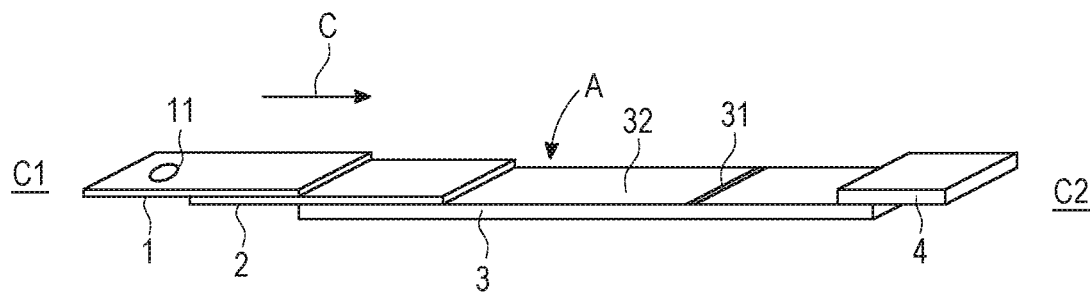
FIG. 1 is a schematic perspective view of an exemplary internal structure of the heart-failure detection device according to an embodiment of the present invention.
Figure 2:
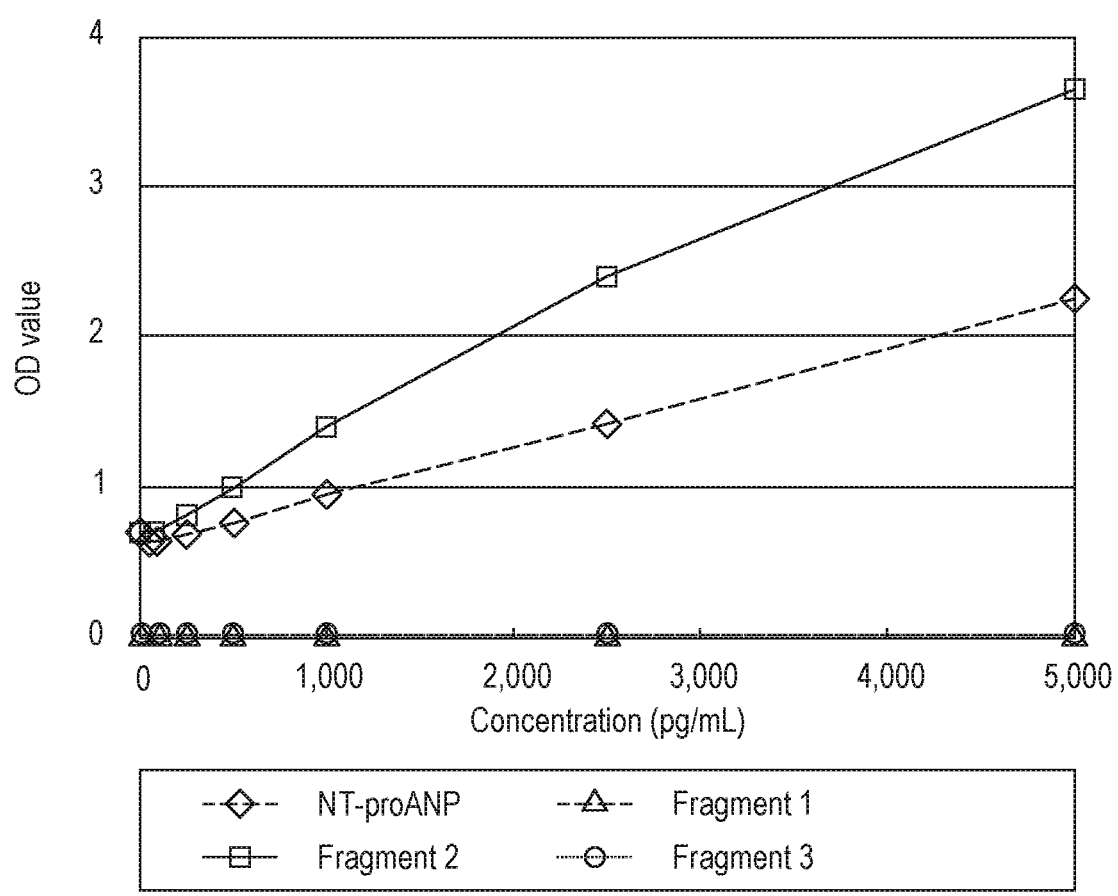
FIG. 2 is a graph illustrating the results from sandwich ELISA using antibodies produced from hybridoma established in Example 1.

1 Sample application portion
2 Labelled-antibody retention portion
3 Measurement portion
4 Absorption portion
A Heart-failure detection device
C Flow path
C1 Upstream side
C2 Downstream side

The invention claimed is:

1. A method of detecting heart failure from a sample collected from an organism, the method comprising the step of:
   capturing NT-proANP or a fragment thereof contained in the sample using a first antibody for which a first epitope lies on any site among positions 31 to 67 of an amino acid sequence of NT-proANP;
   adding a second antibody for labeling for which a second epitope lies on any site among positions 31 to 67 of the amino acid sequence of NT-proANP;
   measuring a level of NT-proANP or a fragment thereof in the sample; and
   detecting heart failure based on the level of NT-proANP or a fragment thereof in the sample,
   wherein each of antibody A, antibody B and antibody C comprises a heavy chain variable domain (VH) and a light chain variable domain (VL), and each VH and VL comprises three complimentary determining regions (CDR), CDR1, CDR2, and CDR3;
   wherein antibody A comprises a VH having CDR1 as set forth in SEQ ID NO: 5, CDR2 as set forth in SEQ ID NO:6, and CDR3 as set forth in SEQ ID NO:7, and a VL having CDR1 as set forth in SEQ ID NO:8, CDR2 as set forth in SEQ ID NO: 9, and CDR3 as set forth in SEQ ID NO:10;
   wherein antibody B comprises a VH having CDR1 as set forth in SEQ ID NO: 15, CDR2 as set forth in SEQ ID NO:16 and CDR3 is VY and a VL having CDR1 as set forth in SEQ ID NO:18, CDR2 as set forth in SEQ ID NO:19, and CDR3 as set forth in SEQ ID NO:20;
   wherein antibody C comprises a VH having CDR1 as set forth in SEQ ID NO: 25, CDR2 as set forth in SEQ ID NO:26, and CDR3 as set forth in SEQ ID NO: 27, and a VL having CDR1 as set forth in SEQ ID NO:28, CDR2 as set forth in SEQ ID NO:29; and CDR3 as set forth in SEQ ID NO:30; and
   wherein the first antibody and second antibody are each selected from the group consisting of antibody A, antibody B and antibody C, and the first antibody is different from the second antibody.

2. The method of detecting heart failure according to claim 1, wherein NT-proANP or a fragment thereof contained in the sample is measured by immunochromatography.

3. The method of detecting heart failure according to claim 2, comprising the steps of:
   applying the sample in an upstream side of a flow path along which a liquid develops due to capillarity, and
   allowing the sample to pass through, in this order, a first region where the second antibody labelled with a labeling substance is retained and a second region where the first antibody is fixed on the flow path while allowing the liquid to develop from the upstream side to a downstream side along the flow path.

4. The method of detecting heart failure according to claim 1, wherein canine, feline, or human heart failure is detected.

5. The method of detecting heart failure according to claim 1, further comprising treating the detected heart failure.

6. The method according to claim 1, wherein the first antibody is antibody A or antibody B, and the second antibody is antibody B or antibody C.

7. A heart-failure detection device for detecting heart failure by an immunochromatography method according to claim 1 applying a sample collected from an organism on a flow path along which a liquid develops through capillarity, wherein the flow path comprises, in this order from an upstream side,
   (1) a sample application portion on which the sample is to be applied,
   (2) a labelled-antibody retention portion for retaining a second antibody labelled with a labeling substance, and
   (3) a measurement portion as a body portion formed with an elongated member in which a first antibody for capturing is fixed substantially linearly at a predetermined location of the elongated member in a substantially vertical direction relative to the longitudinal direction, and
   first and second epitopes for both of the first and second antibodies residing on any site among positions 31 to 67 of an amino acid sequence of NT-proANP,
   wherein each of antibody A, antibody B and antibody C comprises a heavy chain variable domain (VH) and a light chain variable domain (VL), and each VH and VL comprises three complimentary determining regions (CDR), CDR1, CDR2, and CDR3;

wherein antibody A comprises a VH having CDR1 as set forth in SEQ ID NO: 5, CDR2 as set forth in SEQ ID NO:6, and CDR3 as set forth in SEQ ID NO:7, and a VL having CDR1 as set forth in SEQ ID NO:8, CDR2 as set forth in SEQ ID NO: 9, and CDR3 as set forth in SEQ ID NO:10;

wherein antibody B comprises a VH having CDR1 as set forth in SEQ ID NO: 15, CDR2 as set forth in SEQ ID NO:16 and CDR3 is VY and a VL having CDR1 as set forth in SEQ ID NO:18, CDR2 as set forth in SEQ ID NO:19, and CDR3 as set forth in SEQ ID NO:20;

wherein antibody C comprises a VH having CDR1 as set forth in SEQ ID NO: 25, CDR2 as set forth in SEQ ID NO:26, and CDR3 as set forth in SEQ ID NO: 27, and a VL having CDR1 as set forth in SEQ ID NO:28, CDR2 as set forth in SEQ ID NO:29; and CDR3 as set forth in SEQ ID NO:30; and wherein the first antibody and second antibody are each selected from the group consisting of antibody A, antibody B and antibody C, and the first antibody being different from the second antibody.

8. The device according to claim 7, wherein NT-proANP or a fragment thereof contained in the sample is measured by immunochromatography.

9. The device according to claim 7, wherein the device is configured to detect canine, feline, or human heart failure.

10. The device according to claim 7, wherein the device is configured to detect canine heart failure.

* * * * *